United States Patent [19]

Moore et al.

[11] 3,973,852

[45] Aug. 10, 1976

[54] METHOD AND APPARATUS FOR MEASURING PARTICULATE CONCENTRATION IN THE ATMOSPHERE

[75] Inventors: Zack J. Moore; John V. Goode, Jr., both of Lake Jackson, Tex.

[73] Assignee: The Dow Chemical Company, Midland, Mich.

[22] Filed: Aug. 30, 1974

[21] Appl. No.: 501,933

[52] U.S. Cl. ............................ 356/207; 250/552; 250/564; 250/573; 356/186; 356/201; 356/208; 331/94.5 S
[51] Int. Cl.² .................. G01N 21/12; G01N 21/26
[58] Field of Search ........... 356/103, 186, 190, 201, 356/207, 208; 250/564, 573, 552

[56] References Cited
UNITED STATES PATENTS

| | | | |
|---|---|---|---|
| 3,419,333 | 12/1968 | Towner | 356/205 |
| 3,655,289 | 4/1972 | Walker | 356/201 |
| 3,711,210 | 1/1973 | Krukowski | 356/201 |

Primary Examiner—Vincent P. McGraw
Attorney, Agent, or Firm—M. W. Barrow; B. G. Colley; S. S. Grace

[57] ABSTRACT

A method and portable apparatus for measuring particulate concentration in the atmosphere utilizing uniform laser pulses to traverse the atmosphere to be measured and a photo-electronic receiver which discriminates against stray light and detects the attenuation of the laser pulses. This attenuation is caused by particulates in the atmosphere which tend to scatter or absorb light. By using monochromatic laser pulses having wavelengths lying in transparent atmospheric windows, error is not introduced by the attenuation of the beam due to gases occurring naturally in the atmosphere including water vapor. Thus concentration of particulates such as smoke, fog, smog, dust and the like are measurable.

13 Claims, 3 Drawing Figures

METHOD AND APPARATUS FOR MEASURING PARTICULATE CONCENTRATION IN THE ATMOSPHERE

BACKGROUND OF THE INVENTION

With the advent of the increased awareness of the need for pollution abatement, and abatement of atmospheric particulte pollution in particular with regards to this invention, there has developed a need for a transmissiometer which is both portable and accurate to measure atmospheric pollution such as smoke, dust, smog, fog, haze and the like.

By portable, it is meant that there needs to be a transmissometer which can be located and relocated within a matter of a few hours if necessary, and moreover that it be capable of operating off of its own small portable power source, such as batteries, independent of normal commerical electrical transmission line outlets.

By accurate, it is meant that there need be a transmissometer which measure substantially only the particulates in the atmosphere and not the gases occurring naturally in the atmosphere including water vapor. Water vapor varies the same as humidity varies throughout the day and night, and the inclusion of this factor into the output measurement when only particulate concentration is attempted to be measured would introduce unacceptable error into the output measurement. Also to be accurate such a transmissometer must be capable of discriminating against stray light (light from sources other than the transmissometer source).

An examination of the physical laws governing optical attenuation discloses that the resultant signal strength at a distal point of a polychromatic non-collimated light source is a function of the path length and the photon absorption and scatter by the matter in the path beam between the source and the distal point. Thus to accurately measure the attenuation due to particulates in the atmosphere with a smaller power source as much of the light as possible irradiated from the source should be collected by a measuring device located at the distal point. This can be partly achieved by focusing with classical optical lens; for example, the transmissometers used at airports in measuring visibility focus with optical lens.

There has long existed transmissometers at airports to measure visibility, particularly visibility in fogs. These transmissometers usually comprise a comparatively large source light, such as an airport landing light (which requires a large power input) emitting a beam of polychromatic light optically focused on a receiver located a short distance away, at the most a very few hundred feet away. To discriminate against stray light a large long bulky collimating tube is usually placed on the receiver. This necessitates heavy foundations, usually concrete, to keep the receiver focused on the source. Thus the large power requirements and heavy foundation negates the airport transmissometer for use as a portable transmissometer. Furthermore, such a device when used to measure particulates in the atmosphere errs greatly when going from daylight to darkness. This is due to its inability to discriminate to a large enough extent against sunlight.

To overcome some of these deficiencies in the measuring atmospheric particulate concentrations the use of some lasers as light sources has been investigated; for example, the helium neon plasma type laser has been investigated. These plasma laser type transmissometers suffer from their inability to produce lifht of uniform intensity. This results in the requirement that the beam to be used in measuring be chopped and part of it sent to a nearby electronic receiver and comparator to be compared with the part of the beam transmitted through the atmosphere to be measured. This necessity to divert the laser beam into two different paths and bring them back together for comparison, requires chopping equipment and extra optical devices, all of which require more time and labor in moving and setting up. Moreover, for any extended periods of testing a gas-discharge laser requires accessability to a commercial power source or an unacceptably large portable power source. This reduces portability.

Although the gas-discharge light source greatly reduces the amount of power needed when compared to a heated wire source (as used in conventional airport transmissometers) to produce the same irradiance (power density) at a distal point, nevertheless, this power requirement is still too large and there is still too much equipment to be moved and time spent in moving a gas discharge laser for it to be considered truly portable.

In order for there to be measurable quantities of energy at the distal point, a light source of high irradiance must be used. However, this source must be physically small for long-distance focusing purposes. Also, the source can only require a small amount of energy in order for the power source to be portable.

For accurate measurement of atmospheric particulates a transmissometer needs to discriminate against stray light such as the sun's radiation. Measurements should not be effected by time of day or night. It must also be designed such that the absorption of the light by the gases occurring naturally in the atmosphere, and especially the light absorbed by the water vapor in the atmosphere, has virtually no effect on the accuracy of the transmissometer's measurement of particulates in the atmosphere.

These criteria have been achieved by the present invention.

SUMMARY OF THE INVENTION

This invention relates to a portable apparatus and method for measuring particulate concentration in the atmosphere. Uniform laser pulses are rapidly emitted from a portable laser source from which they traverse the atmosphere to be measured for particulate concentration and then impinge upon a photo-electronic detector, said detector being capable of discriminating against stray light. Error from absorption by natural atmospheric gases and especially water vapor is avoided by utilizing laser pulses having a wavelength which lies in a non-absorbing atmospheric window. Thus attenuation of the laser pulses used is proportional to the concentration of particulates in the atmosphere which scatter or absorb some photons of the laser pulses preventing their reaching the receiver. Measurement of the variations in the attenuation of these uniform pulses give an accurate measurement of particulates in the atmosphere over a distance of up to several thousand feet.

DETAILED DESCRIPTION OF THE INVENTION

Figure 1:
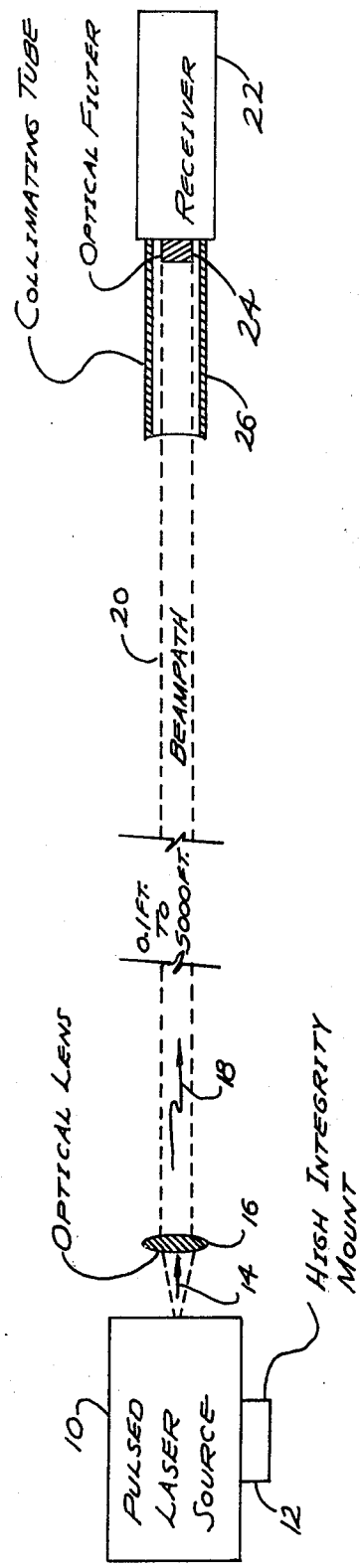
FIG. 1 is a general diagramatic view of the major components of a transmissometer made in accordance with this invention.

This invention relates to a method and an apparatus, hereinafter referred to as a transmissometer, for measuring the concentration of particulates such as smoke, smog, fog, dust, haze, and the like in the atmosphere. A more accurate particulate concentration measurement can be made using this invention even though the equipment used is portable.

Problems considered and resolved in discovering this invention are:

1. In order to be portable the equipment has to be light and easily mounted. Among other things this requires an apparatus and method utilizing a small, portable power source.

2. The apparatus used must be capable of delivering light of intense irradiance if photon scatter and absorption by the particulates is going to be the method used to measure the particulate concentration.

3. The apparatus used in measuring the particulate concentration must be capable of discriminating against stray light (light from sources other than that emitted by the transmissometer).

4. The light used by the transmissometer must be of wavelengths such that such light is only minimally absorbed by the gases comprising the natural atmosphere. This is particularly necessary for wavelengths absorbed by water vapor in the atmosphere, because water vapor concentration varies to such a large extent.

Problems 1 and 2 above are solved by using a semiconductor laser light source. Problem 3 is partially solved by using an optical filter which transmits only light of wavelength approximately the same as the mono-chromatic light emitted by a laser. Additional discrimination is provided against these sources, such as the sun, which radiate light having the same wavelength as that emitted by the laser diode. Such discrimination can be achieved by using light pulses which produce A-C voltage pulses in the receiver circuit as opposed to the essentially D-C voltages produced by the essentially constant radiation from sources such as the sun. Semiconductor laser diodes can be pulsed at a fast enough rate to produce continuous monitoring of the atmosphere. Other lasers can not be pulsed at either a rapid enough rate or with a uniform output to provide useful and accurate measurements. The fact that semiconductor laser diodes can be pulsed satisfactorily and, moreover, produce uniform pulses allows for greater portability of an apparatus, such as a transmissometer, and for greater simplicity in the apparatus design. This is so because uniform pulses allows the use of a light measuring means which does not have to constantly compare the magnitude of the pulse attenuated by particulates in the atmosphere with an unattenuated pulse having the same magnitude that the attenuated pulse had before attenuation. This greatly reduces the amount of equipment required.

The laser light pulses will be uniform only when using uniform electric current pulses to pulse the laser diode and by having the laser diode at the same temperature each time a light pulse is emitted.

Finally to solve problems 4 above there must be available laser diodes which emit radiant pulses of wavelengths which fit in the non-absorbing wavelength bands of the atmosphere hereinafter referred to as "atmospheric windows".

All of these conditions must be met by the same transmissometer in order to be portable and accurate.

The method and apparatus of this invention meet all of these conditions, for a method and portable transmissometer have now been discovered for measuring particulate concentration in the atmosphere, the transmissometer comprising a small pulsed laser source which emits monochromatic laser pulses of uniform energy magnitude whose wavelength lies within one of the essentially non-absorbing wavelength windows of the atmosphere; such pulses being directed through the atmosphere to be measured for particulate concentration toward a receiver; such receiver having a light filtering means which responds only to light having wavelengths nearly the same as that wavelength of the monochromatic laser pulses emitted by the source; and said receiver having a linear semiconductor detector diode as part of the receiver's electronic circuit; said semiconductor detector diode causing a small voltage to appear at the input of a voltage amplifying circuit to which the diode is A-C coupled; said amplifying circuit linearly amplifying said voltage pulse sufficiently to produce pulses capable of being handled by a peak detector circuit electrically connected to the amplifier circuit's output; the voltage output of the peak detector circuit being the signal to a suitable recording device.

Referring to the drawing, FIG. 1 illustrates a pulsed laser source 10 which produces non-collimated but uniform laser pulses 14 (laser pulses being inherently monochromatic and coherent). To source 10 can be attached a shield (not shown) for protection against the elements. A similar shield (not shown) can be attached to the receiver 22. The non-collimated laser pulses 14 are directed toward receiver 22 and need pass through the optical lens 16 for distances between source 10 and receiver 22 of more than about 50 ft. The transmissometer of this invention is capable of operating over a range of from about 0.1 ft. to about 5000 ft. distance between the source 10 and receiver 22. A more preferred distance is from about 50 ft. to about 500 ft.

For more applications the optical lens 16 is used to collimate the non-collimated laser pulses 14 into collimated laser pulses 18. Lens 16 is located at such a distance from semiconductor laser diode 30, shown in FIG. 2, such that semiconductor laser diode 30 is at the focal point of lens 16. The beampath 20 of the pulses 18 traverses the atmosphere in which particulate concentration is to be measured, the pulses being attenuated by the presence of particulates which tend to scatter and absorb photons, and ultimately reach the receiver 22. Beampath 20 is shown as having no divergence, but in actuality all light beams, including lasers, ultimately diverge somewhat. Thus, in actuality, beampath 20 has spreadout by a few diameters once it reaches receiver 22 if the receiver 22 is located several hundred feet from source 10. A simple geometric consideration of this fact shows that slight movement of receiver 22 in this slightly divergent beampath 20 will not remove the receiver 22 from the beampath 20. Thus the receiver 22 needs no high integrity mounting means to prevent it from slight movement. However, this is not true for the source 10 which needs a high integrity mount 12 to minimize slight movement. Even though the beampath 20 slightly diverges, slight movements of source 10 result in much larger movements of the beampath 20 at the receiver 22.

To discriminate against light of wavelenghts different from that of the monochromatic laser pulse 18, an optical filter 24 is mounted on the front of the receiver 22 such that all light entering the receiver 22 must pass through filter 24. Two kinds of filters may be used for filter 24. They are the sharp cut-off blocking filter type and the optical bandpass filter type. The latter is generally preferred. To aid in the discrimination against stray light, a collimating tube 26 may be mounted on the entrance of receiver 22, surrounding the lens 24, and directed parallel to the beampath 20. Discriminating against stray light having the same wavelenght as the laser pulses 18 will be discussed below. For normal use such as use where the receiver does not have to receive direct or near direct sunlight, the transmissometer and method of this invention measures atmospheric particulate concentration irregardless of the time of day or night.

Figure 2:
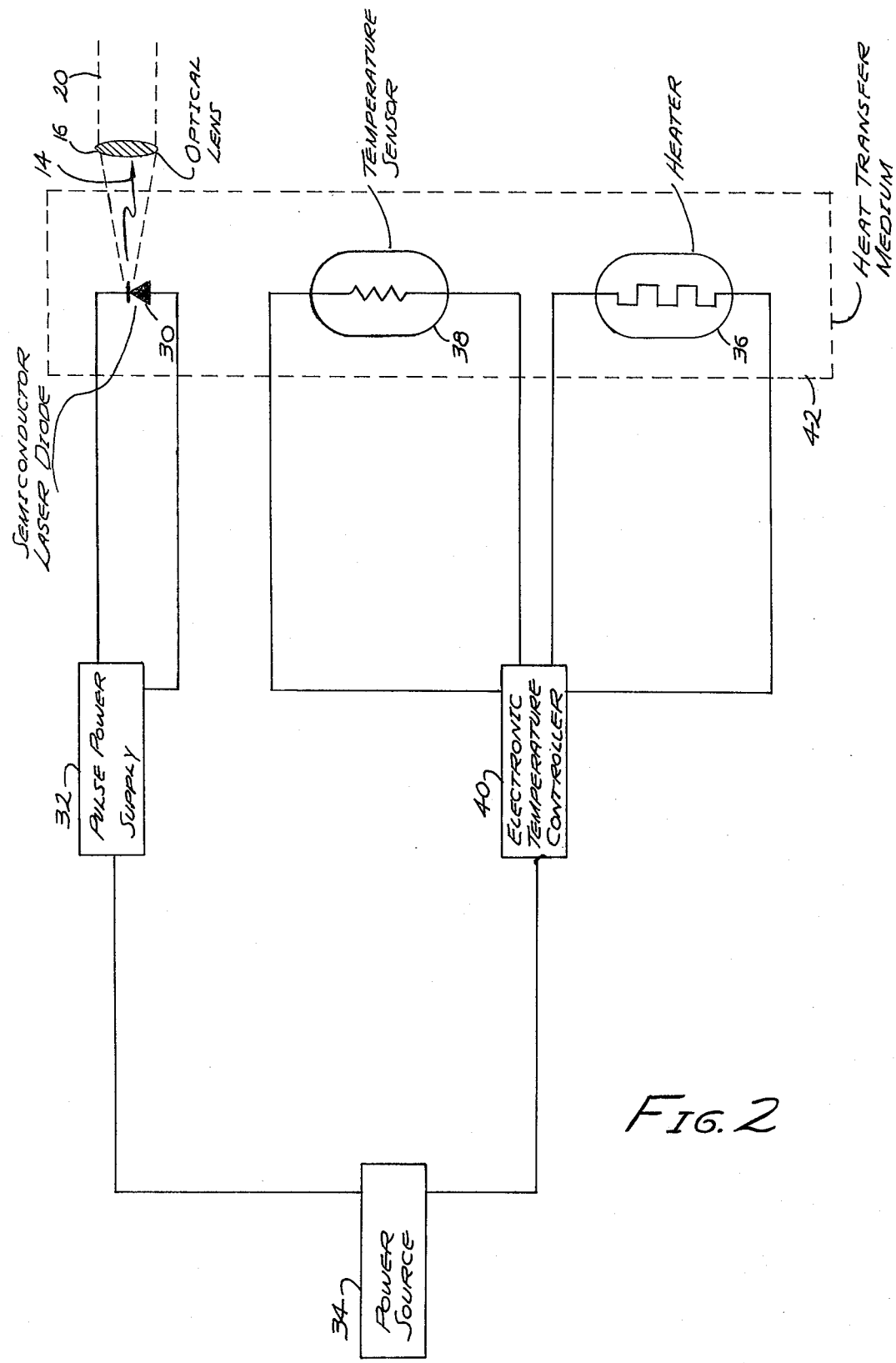
FIG. 2 is a more detailed diagramatic view of the Pulsed Laser Source shown in FIG. 1.

Referring to FIG. 2 of the drawing, the source 10 is shown to be comprised of semiconductor laser diode 30, a pulse power supply 32, a small power source 34, a heater 36, a temperature sensor 38, an electronic temperature controller 40, and a heat transfer medium 42. The laser diode 30 is current pulsed by a pulse power supply at a rate of from about 10 pulses per second to about 1000 pulses per second. A preferred rate is from about 200 pulses per second to about 500 pulses per second. The pulses can have a half-peak width of from about 1 nanoseconds to about 1000 nanoseconds with a preferred half-peak width of from about 5 nanoseconds to about 500 nanoseconds. These current pulses cause the laser diode 30 to emit light pulses 14 at the same time rate as the current pulses and of the same half-peak width. The pulse power supply 32 derives its electrical power from the power source 34 which can be a battery.

To maintain uniformity of magnitude or energy level of the laser pulses 14 which is crucial to the successful operation of this invention, the temperature of the laser diode 30 should be same at the beginning of each pulse. The temperature is set somewhat above ambient. Temperature control is achieved by first thermally cross-coupling the laser diode 30, the heater 36, and the temperature sensor 38 through a heat transfer medium 42 such as magnesium metal, and secondly by the interaction of the heater 36, the temperature sensor 38, and the electronic temperature controller 40 to which the temperature sensor 38 and the heater 36 are electrically connected. The temperature sensor 38 should be embedded in the heat transfer medium 42 close to the laser diode 30 in order to achieve better temperature control. Pulse rates should not be so closely time-spaced so as not to allow the laser diode 30 to return to essentially the same temperature as that part of the heat transfer medium 42 which is adjacent to the diode.

After the collimated pulses 18 leave the pulsed laser source 10 and the lens 16 they travel through the atmosphere along beampath 20 being attenuated in amplitude in proportion to the particulate concentration along the beampath 20 and ultimately impinging upon the filter 24 of the receiver 22. The attenuation of the laser pulses 18 is caused by the particulates which scatter and absorb photons. The filter 24 transmits the attenuated laser pulses as well as stray light having wavelenghts the same and nearly the same as that of the attenuated laser pulses 50 striking the semiconductor detector diode as depicted in FIG. 3 of the drawing.

Figure 3:
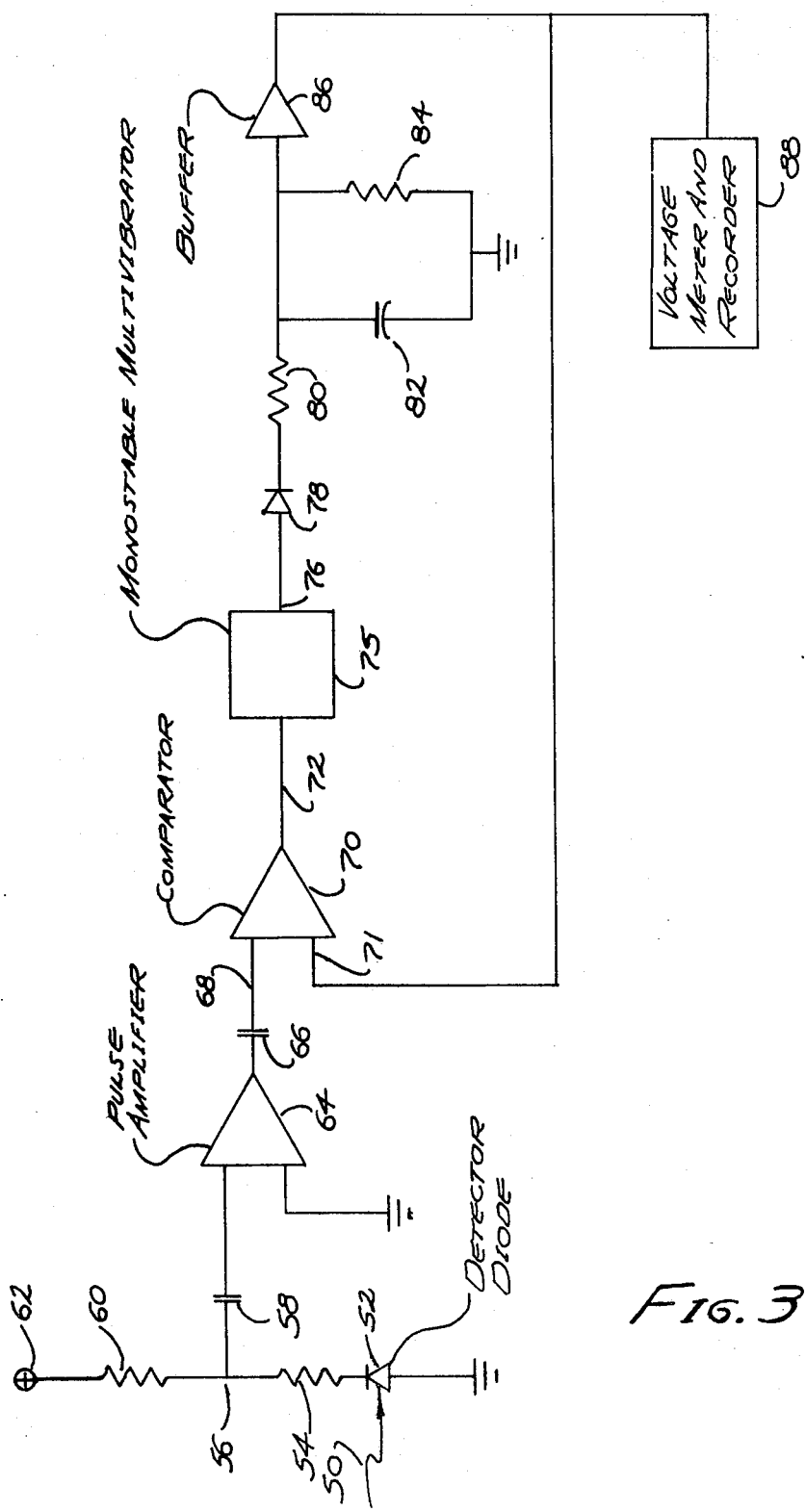
FIG. 3 is a more detailed diagramatic view of the Receiver shown in FIG. 1.

Referring to FIG. 3 of the drawing, the electronic circuitry of the receiver 22 can be observed in diagramatic form. The detector diode 52, resistor 54, resistor 60 and positive D-C voltage source 62 with the detector diode 52 reversed biased and connected to ground comprise a voltage divider circuit. The negative junction of dectector diode 52 is connected to resistor 54 which is connected through node 56 to an A-C coupling capacitor 58 and resistor 60 which is connected to the positive D-C voltage source 62. When there is no light impinging upon detector diode 52 there is virtually no current flow through the voltage divider circuit. Thus the voltage at node 56 is virtually the same as that of the positive D-C voltage source 62, but since the voltage at node 56 is D-C there is no voltage signal passed through the A-C coupling capacitor 58 to the pulse amplifier 64. Similarly when a D-C light (a light of constant magnitude or amplitude) is impinging upon the detector diode there appears no signal across the A-C coupling capacitor 58 to the pulse amplifier 64, even though the voltage at node 56 has been lowered because of the current flow then existing in the voltage divider circuit due to the lowered resistance of the detector diode 52 which lowered resistance is caused by and is linearly proportional to the amplitude of the D-C light impinging upon the detector diode 52. However, when an A-C light pulse 50 impinges upon detector diode 52, the accompanying pulse (or A-C) voltage drop appearing at the node 56 is passed across the A-C coupling capacitor to the pulse amplifier 64. This is a way in which the transmissometer of this invention discriminates against stray source D-C light having the same wavelength as the monochromatic A-C laser pulses.

There is one problem caused by this D-C light transmitted by the filter, and that involves the linear dynamic range of the detector diode 52. Although such D-C light does not produce voltage signals at the pulse amplifier 64, it does limit the linear dynamic range of the detector diode. In order for there to be linear dynamic response by the detector diode 52 when both A-C laser pulses and D-C light impinges upon the detector diode 52, the detector diode 52 must have a wide range of linear dynamic response to impinging light irradiance. Even without the presence of D-C light the added feature of having greater precision of the system is increased by having a detector diode 52 with a wide range of linear response. A minimum range of 4 decades is acceptable, a preferred detector diode 52 is one having a linear range greater than about 6 decades, and a more preferred detector diode 52 is one having a linear range greater than about 10 decades.

The Schottky Barrier PIN type and planar diffused PIN type photodiodes are suitable for use as semiconductor detector diode 52. Besides having a linear dynamic range greater than ten decades these two types of detector diodes have their maximum response close to 9100 A, a wavelength in the center of one of the acceptable atmospheric windows. Because of the quick roll-off in response to wavelengths greater than 9100 A by both the Schottky Barrier PIN type diode and the planar diffused PIN type diode, these two diodes can be used in conjunction with a sharp cut-off blocking filter which effectively blocks light of wavelengths less than about 7500 A to produce the same filtering effect as a high band pass optical filter which transmits only a narrow range of wavelengths, cutting off wavelengths on both sides of this transmission band. Normally high band pass optical filters are preferred for this invention to blocking filters which cut-off only light of wavelengths on one side of the transmission band. It should be emphasized that this invention is not limited to using light windows of the atmosphere centered around 9100 A nor to Schottky Barrier PIN layer depletion PIN type diodes for use as the detector diode 52. Other diodes responding to laser pulse wavelengths lying in other atmospheric window wavelength bands can be used.

The A-C voltage drops appearing at node 56 are proportional in amplitude to the light impinging upon detector diode 52. As mentioned above they are fed through an A-C coupling capacitor 56 to a fast high gain voltage pulse amplifier 64 which linearly amplifies the voltage pulse and transmits it through a second A-C coupling capacitor 66 to voltage comparator 70 at comparator input 68. Capacitor 66 is used to prevent any D-C offset voltage drifts of the pulse amplifier 64 from appearing at the comparator input and thus upsetting the amplitude of the voltage pulse from the pulse amplifier 64 which until this point in the circuit still is linearly proportional to the amplitude of the light pulses 50 impinging upon detector diode 52. Comparator 70 comprises a high gain differential amlifier which produces an electronic signal at its output terminal connected to lead 72 whenever the voltage at input 68 exceeds the voltage appearing at input 71 of the comparator 70. Any signal produced by the comparator will be carried along lead 72 to the input of a monostable multivibrator 75 and triggers said multivibrator into producing a precise quantum of electrical energy at output 76. This quantum of electrical energy is the form of a squarewave having a constant voltage amplitude for a fixed period of time. Voltage pulse on the order of 5 volts and lasting in the order of 0.5 milliseconds are acceptable, but these values are not critical. It is critical, however, to this particular mode of the invention that the quantum of energy produced by the multibrator be a fixed amount each time one is produced. The circuit components, diode 78 resistor 80, capacitor 82 and resistor 84 can be described as being a peak detector circuit whose function is to measure the D-C voltage across capacitor 82 as small signals entering the peak detector circuit incrementially increases said voltage, or in the absence of said incoming signals the voltage across capacitor 82 slowly decays toward zero as the capacitor 82 discharges to ground through resistor 84.

The voltage across capacitor 82 is the signal used as being inversly proportional to the particulate concentration of the atmosphere. The capacitor 82 and monostable multivibrator 75 are chosen such that the quantum of energy produced by the multivibrator 75 is small, on the order of 1/10000 th, of the quantum of energy capable of being stored in the capacitor 82. Thus it would take on the order of several hundred pulses from the monostable multivibrator to charge the capacitor up to new voltage level representing a decrease in the atmospheric particulate concentration. At first glance this seems to be unresponsive to changes in the atmospheric particulate concentration, but when it is remembered that the laser pulses 50 are being produced at a rate on the order of about 3 hundred per second it is seen that a record of each pulse is not what is desirable inasmuch as hundreds of changes per second of the atmospheric particulate concentration is not the information desired, but rather more cumulative information is desired. Data points giving the cumulative changes over a few seconds is adequate for measuring atmospheric particulate concentration over a span of time. This type of data is provided by using the voltage across capacitor 82 as a signal inversely indicating particulate concentration of the atmosphere.

A high input resistance buffer 86 and the diode 78 prevents current leakage out of the capacitor 82 - resistor 84 circuit. Thus capacitor 82 is slowly discharged to ground through resistor 84 according to the RC time constant of the resistor 84 and capacitor 82.

The voltage pulse produced by the monostable multivibrator 75 at its output 76 are transferred through diode 78 and resistor 80 to the parallel RC circuit consisting of capacitor 82 and resistor 84. Part of the energy of this voltage pulse is stored in capacitor 82 with the remaining going to ground through resistor 84. Buffer 86 is a high input impedance (high with respect to resistor 84) unity gain voltage amplifier which transmits the voltage across capacitor 82, without leaking the current stored in capacitor 82, to a voltage meter and recorder and also back to the voltage comparator input 71. Thus the voltage across capacitor 82 (and at comparator input 71) is inversely proportional to the particulate concentration of the atmosphere and is determined by the previously arrived pulses.

An increase in the atmospheric particulate concentration will result in a decrease in the irradiance of the laser pulses 50 which will result in decreased voltage pulses at comparator input 68. Thus the voltage at input 68 will be lower than the voltage at input 71. As long as this condition exists there will be no output signal from comparator 70 and thus no triggering of the monostable multivibrator 75 and thus no charging pulses for capacitor 2. Therefore the voltage of capacitor 82 will decay until the voltage at input 71 drops below the voltage at input 68 of the comparator 70.

Correspondingly a decrease in the atmospheric particulate concentration will result in an increase in the irradiance of the laser pulses 50 which will result in there being a higher voltage at input 68. This will cause comparator 70 to trigger monostable multivibrator 75 which will emit an energy pulse incrementally charging capacitor 82. This charging process will continue until the voltage across capacitor 82 and thus the voltage at input 71 equals the voltage at input 68.

The voltage meter and recorder follow these voltage changes across capacitor 82 and thus data can be observed and recorded.

We claim:

1. A portable transmissometer for measuring particulate concentration in the atmosphere over a distance of from about 0.1 ft. to about 5000 ft. comprising a semiconductor laser light diode which emits monochromatic laser light pulses of intense irradiance and uniform energy magnitude when pulsed by a uniform current pulse and when the temperature of the diode is the same at the beginning of each pulse with the wavelength of said laser light pulses lying within one of the essentially non-absorbing wavelength windows of the atmosphere;

a pulse power supply which current pulses the laser diode at a rate of from about 10 pulses per second to about 1000 pulses per second, with the current pulses, and the corresponding light pulses produced by the diode, having a half-peak width of from about 1 nonosecond to about 500 nonoseconds;

a temperature controlling means to have the laser diode at the same temperature at the beginning of each pulse, an optical lens located at such a distance from the laser diode so that its focal point is located at the laser diode so as to collimate the uncollimated laser light pulses, with such pulses being directed through the atmosphere to be measured for particulate concentration toward a receiver, with such receiver having a light filtering means which responds only to light having wavelengths nearly the same as that of the wavelengths of the monochromatic laser pulses emitted by the laser diode; and said receiver having a linear semiconductor detector diode having a linear dynamic response to the light impinging upon it over a range of at least 6 decades as part of the receiver's electronic circuit; said semiconductor detector diode causing a small voltate to appear at the input of a voltage amplifying circuit to which the diode is A-C coupled;

said amplifying circuit amplifying said voltage pulse sufficiently to produce voltage pulses capable of triggering a monostable multivibrator which produces a voltage pulse of a fixed amount of energy each time such a voltage pulse if produced with said monostable multivibrator produced voltage pulses capable of being handled by a peak detector circuit electrically connected to the monostable multivibrator's output; the voltage output of the peak detector circuit being the signal to a suitable recording device.

2. The transmissometer of claim 1 wherein the laser source emits monochromatic pulses of about 9100 angstroms.

3. The transmissometer of claim 1 wherein the distance between the pulsed laser source is from about 50 ft. to about 500 ft.

4. The transmissometer of claim 1 wherein the light filtering means is an optical band pass filter transmitting only that light of wavelengths the same as that of the wavelength of the laser light pulses.

5. The filter of claim 4 wherein transmitted light has a wavelength of from about 7500 A to about 10,000 A.

6. The transmissometer of claim 1 wherein the linear semiconductor diode is a Schottky Barrier PIN photodiode.

7. The transmissometer of claim 1 wherein the linear semiconductor diode is a planar diffused PIN photodiode.

8. The transmissometer of claim 7 wherein the light filtering means is a sharp cut-off blocking filter effectively blocking wavelengths less than about 7500 A.

9. The transmissometer of claim 1 wherein the semiconductor detector diode has a linear dynamic response of at least 10 decades.

10. The transmissometer of claim 1 wherein the pulsed laser source emits pulses at a rate of from about 200 pulses per second to about 500 pulses per second.

11. The method for measuring particulate concentration in the atmosphere by way of an attenuation of light comprising:

emitting uniform semi-collimated laser pulses from a semiconductor laser diode at a rate of from about 10 pulses per second to about 1000 pulses per second;

using an electronic controlled heating system to bring the laser diode back to the same temperature before the emission of the next pulse;

placing the laser diode at the focal point of a simple optical convex lens situated such that the semi-collimated pulses pass through the lens and are collimated thereby;

aligning the laser diode and lens in such a manner so that the collimated laser pulses traverses the atmosphere to be measured for particulate concentration;

using laser pulses of wavelengths which are not absorbed by the gases occurring naturally in the atmosphere including water vapor;

having the laser pulses, which have been attenuated by particulates in the atmosphere, impinge upon a receiver circuit and this having them pass through an optical filter which transmits essentially only that light of the same wavelength as that of the laser pulses emitted by the laser diode;

detecting the light which has transversed the optical filter by a semiconductor detector diode which is electrically connected in an electronic amplifying and peak detector circuit, which circuit by A-C capacitor coupling discriminates against the voltages caused by strong light having the same wavelength as the laser pulses but having greater pulse widths;

linearly amplifying the voltage pulses created by the attenuated laser pulses acting upon the semiconductor detector diode;

feeding the amplified voltage pulses to a voltage comparator which triggers a monostable multivibrator when the input voltage exceeds the voltage fed back from the output of the receiver circuit, the monostable multivibrator producing a square-wave voltage pulse containing the same amount of energy in each pulse;

feeding the voltage pulse through a diode to a parallel capacitor-resistor circuit which is connected to ground, with said voltage pulse incrementally contributing to the voltage on the capacitor said capacitor discharging through the parallel resistor to ground when not being charged; measuring the total voltage across the capacitor which yields a value inversely proportional to the particulate concentration in the atmosphere.

12. A portable transmissometer for measuring particulate concentration in the atmosphere comprising:

a small pulsed semiconductor laser diode, a power source, an electronic pulse power supply, a heater, a temperature sensor, an electronic temperature controller, and a heat transfer medium wherein the power source supplies electrical energy to the electronic pulse power supply which provides uniform electric current pulses to the semiconductor laser diode which emits uniform monochromatic laser pulses of uniform energy magnitude and whose wavelength lies within one of the essentially non-absorbing wavelength windows of the atmosphere, said laser pulses being uniform due to using only uniform current pulses to pulse the laser diode and by having the laser diode at the same temperature each time a light pulse is emitted by having the semiconductor laser diode, the temperature sensor, and the heater thermally connected through the heat transfer medium, with the heater providing the heat necessary to have the laser diode at the same temperature each time a light pulse is emitted, with the heater being controlled by and drawing its electrical power from the electronic temperature controller, with said electronic temperature controller drawing its power from the power source while regulating the heater output by receiving signals from the temperature sensor and comparing these signals with a pre-set temperature signal output means contained within the electronic temperature controller, with such laser pulses emitted by the laser diode being directed through the atmosphere to be measured for particulate concentration toward a receiver, with such receiver having a light filtering means which responds only to light having wavelengths nearly the same as that of the wavelengths of the monochromatic laser pulses emitted by the source; and said receiver having a linear semiconductor detector diode as part of the receiver's electronic circuit; said semiconductor detector diode causing a small voltage to appear at the input of a voltage amplifying circuit linearly amplifying said voltage pulse sufficiently to produce pulses capable of being handled by a peak detector circuit electrically connected to the amplifier circuit's output of the peak detector circuit being the signal to a suitable recording device.

13. A portable transmissometer for measuring particulate concentration in the atmosphere comprising a small pulsed laser source which emits monochromatic laser pulses of uniform energy magnitude and whose wavelength lies within one of the essentially non-absorbing wavelength windows of the atmosphere, with such pulses being directed through the atmosphere to be measured for particulate concentration toward a receiver, with such receiver having a light filtering means which responds only to light having wavelengths nearly the same as that of the wavelengths of the monochromatic laser pulses emitted by the source; and said receiver having a linear semiconductor detector diode as part of the receiver's electronic circuit; said semiconductor detector diode causing a small voltage to appear at the input of a voltage amplyfing circuit to which the diode is A-C coupled by an A-C coupling capacitor which passes on to a pulse amplifier the pulse voltage drop in a voltage divider circuit of which the semiconductor detector diode is a series part and whose resistance drops linearly with the impingement of photons upon it; said pulse amplifier being capable of linearly amplifying several hundred times millivolt voltage pulses as narrow as 10 nanoseconds half-peak pulse width, said pulse amplifier's output being electrically connected to the input of a voltage comparator with said voltage comparator being also electrically connected through a feedback lead to the receiver circuit output, and said comparator emitting a trigger signal to the input of a monostable multivibrator whenever the amplified voltage pulse is greater than the voltage of the receiver circuit output; said monostable multivibrator upon triggering, emitting a predetermined constant energy pulse from its output through a diode to a resistor and capacitor connected in parallel to ground and also connected to a high input resistance buffer, most of the energy from the monostable multivibrator being stored in the capacitor, with the voltage across said capacitor being reflected through the buffer to a linear voltage detecting and recording device.

* * * * *